(12) United States Patent
Xiao et al.

(10) Patent No.: US 7,241,264 B2
(45) Date of Patent: Jul. 10, 2007

(54) VARIABLE-PITCH CAM MECHANISM FOR TENSION DEVICES

(75) Inventors: Jia Hua Xiao, Bridgewater, NJ (US);
Ifung Lu, Forest Hills, NY (US);
Steven Nguyen, Somerset, NJ (US)

(73) Assignee: Ethicon, Inc., Somerville, NJ (US)

( * ) Notice: Subject to any disclaimer, the term of this patent is extended or adjusted under 35 U.S.C. 154(b) by 505 days.

(21) Appl. No.: 10/609,726

(22) Filed: Jun. 30, 2003

(65) Prior Publication Data

US 2004/0267097 A1 Dec. 30, 2004

(51) Int. Cl.
*A61B 1/32* (2006.01)

(52) U.S. Cl. .................. 600/229; 248/222.13; 403/314

(58) Field of Classification Search ................ 600/229, 600/230, 235; 248/160, 276.1, 229, 25, 222.13; 403/314
See application file for complete search history.

(56) References Cited

U.S. PATENT DOCUMENTS

| | | | |
|---|---|---|---|
| 2,510,198 A | 6/1950 | Tesmer | |
| 3,096,962 A | 7/1963 | Meijs | |
| 3,584,822 A | 6/1971 | Oram et al. | |
| 3,858,578 A | 1/1975 | Milo | |
| 5,284,130 A | 2/1994 | Ratliff | |
| 5,348,259 A | 9/1994 | Blanco et al. | |
| 5,513,827 A | 5/1996 | Michelson | |
| 5,662,300 A | 9/1997 | Michelson | |
| 5,816,471 A | 10/1998 | Plyley et al. | |
| 5,899,425 A | 5/1999 | Corey Jr. et al. | |
| 5,947,896 A | 9/1999 | Sherts et al. | |
| 6,254,535 B1 | 7/2001 | Furnish et al. | |
| 6,264,605 B1 | 7/2001 | Scirica et al. | |
| 6,565,508 B2 | 5/2003 | Scirica et al. | |

FOREIGN PATENT DOCUMENTS

WO    WO 01/50946    7/2001

*Primary Examiner*—Eduardo C. Robert
*Assistant Examiner*—David Comstock (57) ABSTRACT

A malleable shaft device for use in surgical procedures, having a tension fiber therein, whereby the malleable shaft transitions from a malleable state to a rigid state when a force is applied to the tension fiber, has a variable-pitch cam operatively connected to the tension fiber, and a lever operatively connected to the variable pitch cam for applying force. The mechanical advantage of the cam changes with displacement to accommodate increasing load, and to increase the rate of travel while loads are light. The force profile may provide for a constant input force to accomplish the full travel of the cam.

22 Claims, 8 Drawing Sheets

FOREARM SUPINATION (A),
PRONATION (B)

VARIABLE-PITCH CAM MECHANISM FOR TENSION DEVICES

BACKGROUND OF THE INVENTION

1. Field of Invention

The invention relates to the field of tension-stiffening devices and surgical instrumentation. More specifically, it relates to a variable-pitch cam mechanism for use in a malleable-shaft surgical retractor, particularly those that have a fiber running through their length and stiffen upon the tensioning of that fiber.

2. Description of Related Art

In the field of medical instrumentation, malleable shaft stabilization devices are known in the art. Particularly in Coronary Artery Bypass Graft (CABG) procedures, such instruments are used to stabilize the surface of the beating heart muscle at the site where the anastomosis will be formed. The instruments will have a malleable shaft of a certain length, with a stabilizer foot at a distal end. The shaft can be positioned as required, then a lead screw at a proximal end is turned by some manner of handle. The turning of the lead screw applies tension to a fiber, such as a metal wire or braided cable. The tensioning of the cable compresses the malleable shaft, and secures it rigidly into position. These devices are considered an improvement over other stabilizers, because the length of the shaft can be positioned away from the surgical field, as compared to fixed-arm stabilizers that may impede access and vision. With a malleable shaft stabilizer, the surgeon's hands are free to perform another task, and/or the surgical field is clear of obstruction.

These devices are not without drawbacks, however. Among these are the difficulties with the tensioning method. When tensioning the fiber, the forces on the fiber are relatively light as tension is first applied, but comparatively higher at the end of the range, typically approximately 150 lbs. or more. However, the nature of a lead screw is that it has a constant mechanical advantage at all times. The lead screw must then be designed with a great mechanical advantage to accommodate the high forces at the end of the range. Consequently, the pull per turn is reduced. Several turns of the screw are therefore required. It is not uncommon for between 4 and 6 full turns of the screw to be required in order to transition the device from a malleable state to a rigid state. This process is tedious, tiring, and time-consuming.

Moreover, during the time required to transition the malleable shaft into a rigid state, the position of the stabilizer positioned on an end of the malleable shaft may drift on the surface of the heart. To overcome this, it is also not uncommon for the surgeon to position the retractor and hold it in place, and then instruct an assistant to turn the handle the several turns required to tension the shaft.

BRIEF SUMMARY OF THE INVENTION

In order to overcome these and other problems in the prior art, it would be desirable to have a cam mechanism that can accomplish the transition from malleable to rigid states in a smaller motion, while comfortably handling the accompanying loads. It would also be desirable to accomplish the transition while maintaining a constant input force over the range of motion of the actuator.

Therefore, provided by the present invention is a malleable shaft device for use in surgical procedures, having a tension fiber therein, whereby the malleable shaft transitions from a malleable state to a rigid state when a force is applied to the tension fiber, has a variable-pitch cam operatively connected to the tension fiber, and a lever operatively connected to the variable pitch cam for applying force. The mechanical advantage of the cam changes with displacement to accommodate increasing load, and to increase the rate of travel while loads are light. The force profile may provide for a constant input force to accomplish the full travel of the cam. The force profile can provide for the full travel of the cam in a limited range of motion, for example one full turn, one-half turn, or within the range of motion of the longitudinal turning of a human forearm for some portion of the population.

Moreover, according to the present invention, the cam may be transformed into any of several actuation modalities by transforming the cam profile, for example from a cylindrical cam to a linear cam. Also provided by the present invention is a plural-stage device that has varying mechanical advantages among the plural stages.

BRIEF DESCRIPTION OF THE DRAWINGS

These and other features, benefits and advantages of the present invention will become apparent with reference to the following specification and accompanying drawing, in which like reference numerals indicate like features across the several views.

DETAILED DESCRIPTION OF THE INVENTION

Figure 1:
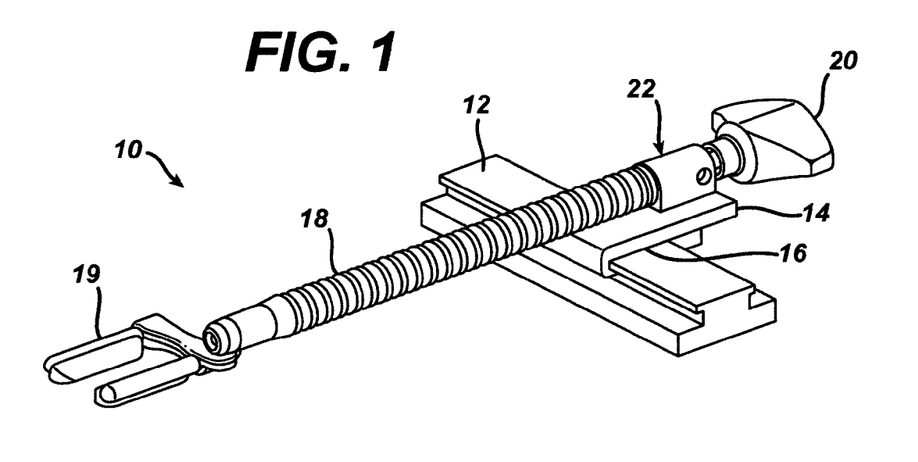
FIG. 1 illustrates a malleable shaft surgical device including a variable pitch cam according to the present invention.

Referring now to FIG. 1, shown is a first embodiment of a malleable shaft device 10. In this case, the device is attached to a rib retractor 12, also commonly used in thoracic surgeries. The malleable shaft device 10 has a base 14, which can include a slot 16 for attachment to another device such as retractor 12. Extending distally from the base 14 is a malleable shaft 18. The malleable shaft 18 will typically have an operative tool such as a stabilizer foot 19, alternately a retractor blade, or other attachment at a distal end thereof. Internal to the malleable shaft 18 is a tension fiber (not shown) that may be a single- or multi-strand wire, braided cable, or other suitable element and material. Extending proximally from the base 14 is a handle 20 for turning the variable-pitch cam 22, located generally internal to the base 14. The variable-pitch cam 22 is operatively connected to the tension fiber.

Figure 2:
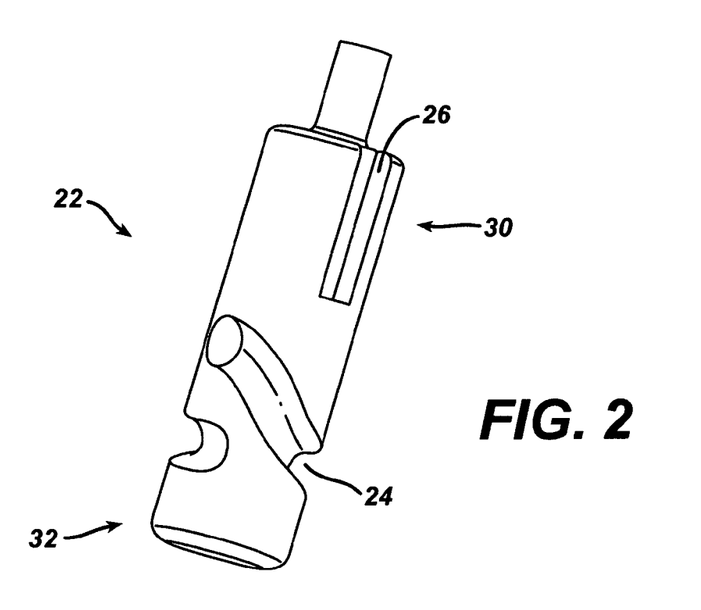
FIG. 2 illustrates a first embodiment of the variable pitch cam according to the present invention.

Referring now to FIG. 2, shown is a cylindrical cam 22 according to a first embodiment of the present invention. The cylindrical cam 22 has a cam slot 24 formed along its circumference. Cam 22 may also include a keyway 26 at a proximal end 30. The keyway can be provided for the attachment of a torque-applying element, such as handle 20 (See, FIG. 1). The tension fiber (not shown) is operatively connected at a distal end 32 of the cam 22.

The cam profile of the present invention can be defined in one of a variety of ways. Beginning with the geometric relationships $$\frac{dS}{dl} = \tan \alpha$$

$$l = \frac{D}{2}\theta$$

where S is tension fiber displacement at a proximal end, l is the circumference movement of the cam 22, α is the angle of the cam groove measured perpendicular to the direction of S, and D is the diameter of cam 22. Cable force $F_c$ is proportional to the proximal cable displacement S as $F_c = \beta$ S, where β is a constant determined by the design of the malleable shaft portion 18.

In one embodiment, the goal is to produce a constant actuating force regardless of the tension required. In the case of a rotatable cam, the actuating force $F_t$ is tangent to the cable force $F_c$, and is given by $$F_t = F_c \tan \alpha = F_c \frac{dS}{dl} = \beta S \frac{dS}{dl}$$

Where $F_t$ is constant, the equation yields $$\beta S dS = F_t dl$$

$$S^2 = \frac{2F_t}{\beta}l = \frac{F_t D}{\beta}\theta$$

In this case, S=0 when l=0, so $$l = \frac{\beta S^2}{2F_t}; \theta = \frac{\beta S^2}{F_t D}$$

A further object of the present invention is to accomplish the full travel, $S_{max}$, of the tension fiber in a much smaller angular displacement than currently required by the prior art. Preferably, the full travel of the tension fiber is accomplished in less that one full turn of the cam ($2\pi$). More preferably, the cam will accomplish the full travel of the tension fiber in less than one half turn ($\pi$). Alternately, the cam will accomplish the full travel of the tension fiber within the typical range of motion of the longitudinal turning of a human forearm.

Taking the case of accomplishing the full travel of the tension fiber in less than one half turn, $$S = S_{max}; 0 \leq \pi$$

which requires $$F_t \geq \frac{\beta S_{max}^2}{2l} = \frac{\beta S_{max}^2}{D\theta}$$

and $$\tan \alpha = \frac{dS}{dl} = \frac{F_t}{\beta S} = \frac{S}{2l} \text{ or } \tan \alpha = \frac{dS}{dl} = \frac{F_t D}{\beta S D}$$

$$S^2 = \frac{2F_t}{\beta}l = \lambda l = \gamma \theta \text{ where } \lambda = \frac{2F_t}{\beta} = const.;$$

$$\gamma = \frac{F_t D}{\beta} = const.$$

$$S(l) = \sqrt{\frac{F_t l}{\beta}}; S(\theta) = \sqrt{\frac{F_t D \theta}{\beta}}$$

Figure 3A:
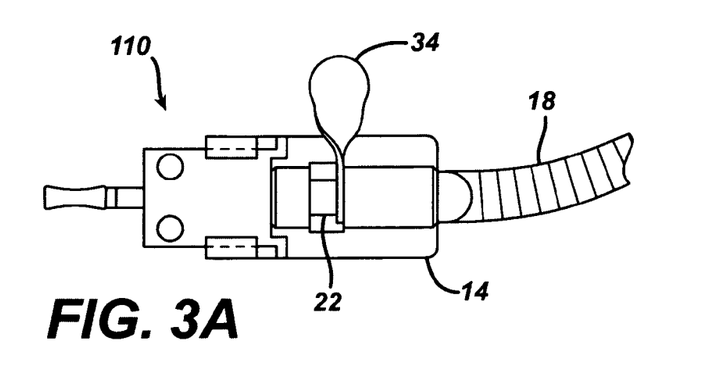
FIGS. 3A through 3C illustrate a second embodiment of the present invention in three mutually orthogonal views.
Figure 3B:
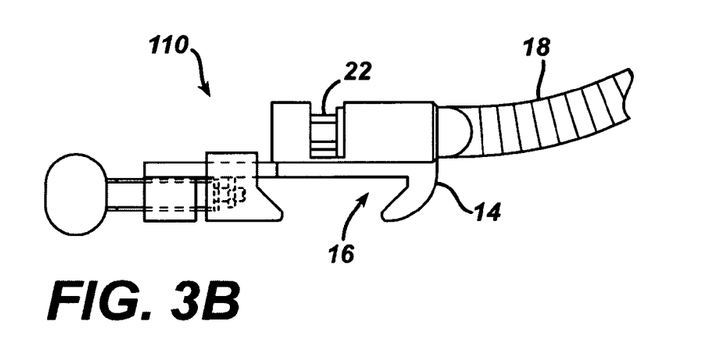
Figure 3C:
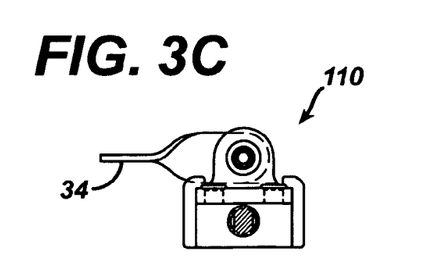

Referring now to FIGS. 3A, 3B and 3C, a second embodiment 110 of the present invention is shown in three orthogonal views, respectively. In this second embodiment 110, the activation lever 34 is operatively connected along the length of cam 22, though it may also be positioned at a proximal end thereof, similar to the first embodiment, supra. This embodiment is particularly advantageous when used in combination with the cam profile described above, wherein the full travel ($S_{max}$) of the tension fiber is accomplished in one-half full turn ($\pi$) of the cam 22.

Figure 7:
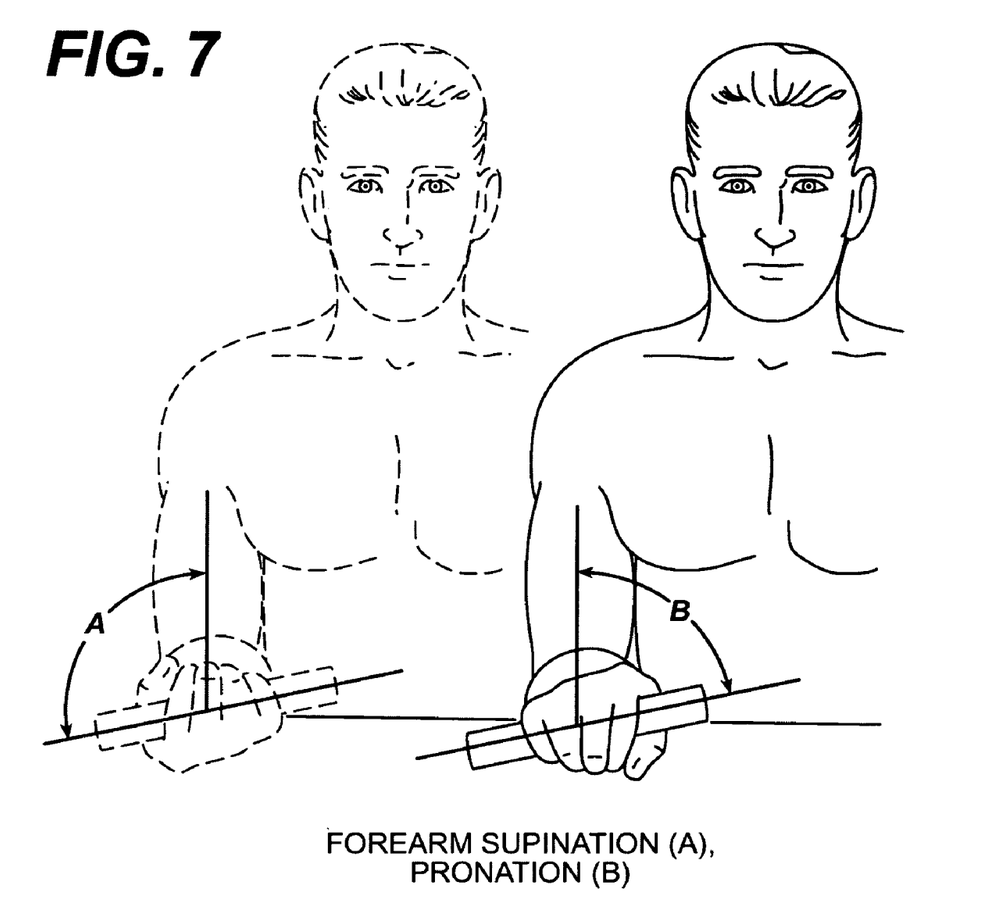
FIG. 7 illustrates the dimensions of rotation of the human forearm taken into account in the design and practice of the present invention.

Alternately, the cam can be designed to accomplish the full travel ($S_{max}$) of the tension fiber within the range of motion of the longitudinal turning of a human forearm. It would be advantageous for a surgeon to be able to transition the malleable shaft to a rigid state in one motion. Data quoted from Human Factors Design Handbook, 2d Ed., Woodson, et al. (McGraw Hill, 1992) by the National Institute of Science and Technology indicates that among male Air Force personnel, the average range of forearm supination and pronation (See FIG. 7) are 113 and 77 degrees, respectively, with standard deviations of 22 and 24 degrees, respectively. Therefore, one can expect half the population to be able to accomplish at least 190 degrees of rotation about the long axis of the forearm in a single motion.

Data such as that quoted can be used to design the cam so that the full travel ($S_{max}$) of the tension fiber is accomplished within the range of motion of the longitudinal turning of a human forearm of some portion of the population. Some allowance can be made to accommodate the expected variance among the human population to accommodate a greater percentage of users. For example, from statistical principles, choosing to full travel to be one standard deviation below the mean, 144° in this case, will allow nearly 85% of users to accomplish the full deflection in a single motion.

Figure 4:
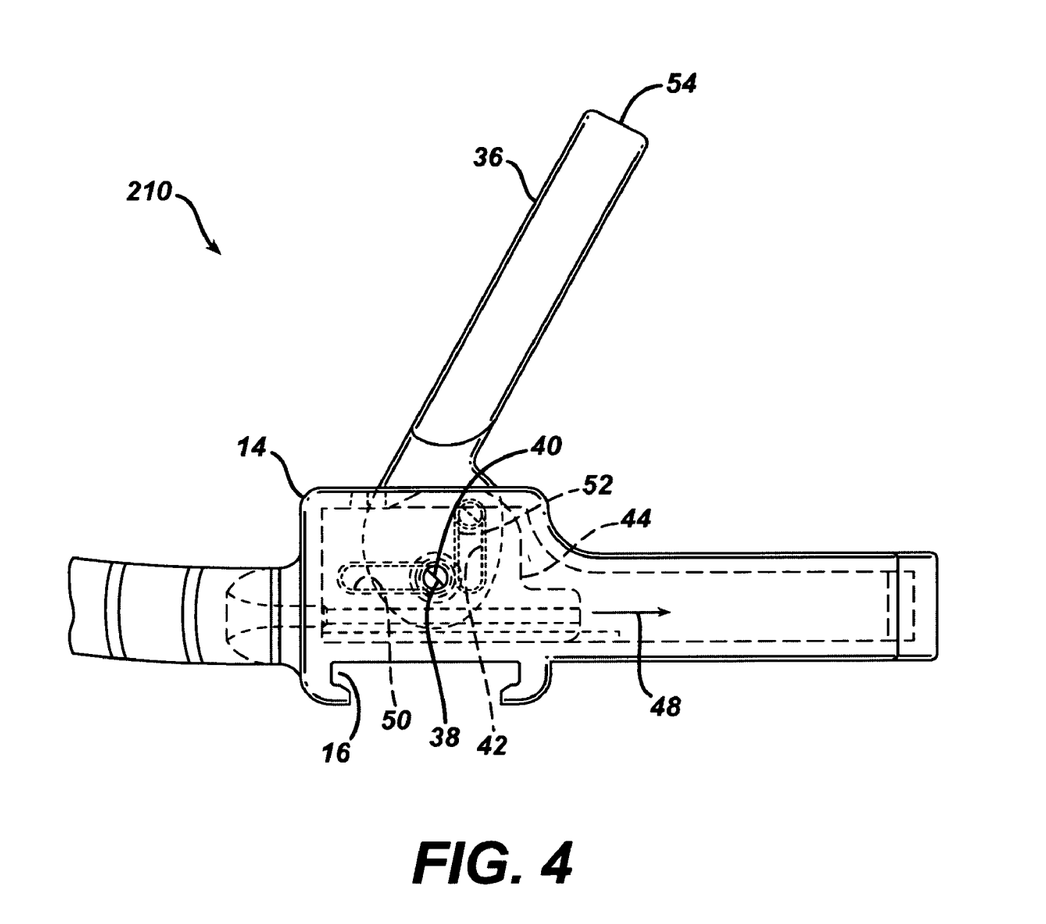
FIG. 4 illustrates yet another embodiment of the present invention having a linear, rather than rotating cam.

An elegant feature of the present invention is that the cam profile may easily be mapped to different activation modalities by a simply transforming the coordinates to the corresponding coordinate system, for example, cylindrical, polar, Cartesian, etc. Referring now to yet another embodiment 210 shown in FIG. 4, shown in partial cross-section. In this embodiment 210, the displacement of the tension fiber (not shown) is accomplished in the same plane as the fiber through a lever action, rather than by a rotating cylindrical cam.

Lever 36 is pivotally attached to the base 14 at a pivot 38. Attached to lever 36 is a follower pin 40, which fits into a cam slot 42 of the cam plate 44. As handle 36 is rotated around pivot 38 in the direction of arrow 46, follower pin 40 moves proximally and downward in slot 42, moving the cam plate 44 proximally, in the direction of arrow 48. Cam plate 44 also has a clearance slot 50 to allow it to move proximally without interfering with pivot 38.

In this embodiment 210, cam slot 42 is a straight slot. In that case, the mechanical advantage applied will vary as L/l cosθ, where L is the length of lever 36 measured from pivot 38 to its free end 54, l is the length 52 between pivot 38 and follower pin 40, and θ is measured at angle 56 between line 58 perpendicular to length 52 and a vertical line 60. Those skilled in the art will recognize that the advantage increases significantly as the lever approaches the horizontal. This arrangement has shown promise as a simple approximation to substitute for the constant force paradigm discussed above.

Figure 4A:
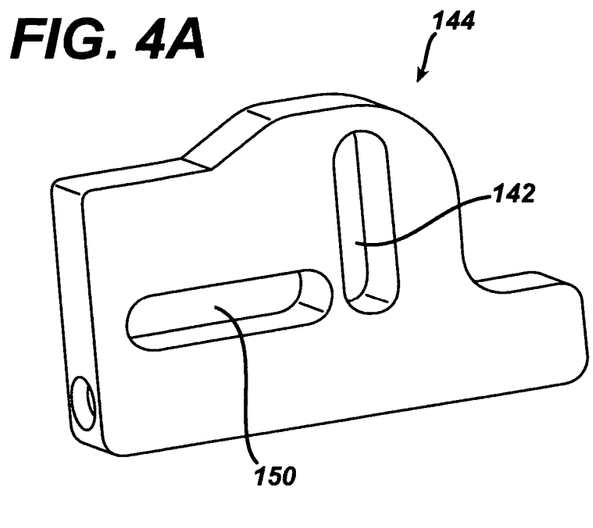
FIGS. 4A and 4B illustrate alternate configurations of the linear cam plate for use with the embodiment of FIG. 4.
Figure 4B:
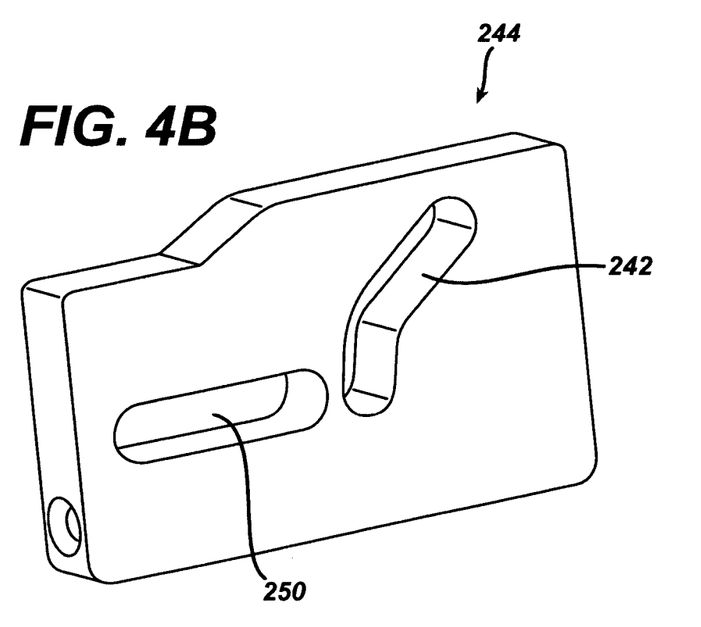

Referring now to FIGS. 4A and 4B, alternate cam plates 144, 244 are shown as a further refinement of the embodiment 210. In cam plate 144, cam slot 142 is cut on an angle, which alters the mechanical advantage only to the extent that the reference line 160 from which θ is measured remains parallel to the long axis of the straight slot 144. In cam plate 244, cam slot 242 varies in angle along its length according to a geometric transformation of the constant force equations discussed above, in a manner apparent to those skilled in the art. Alternately, the profile of cam slot 242 can vary according to another force profile as deemed suitable.

Figure 5:
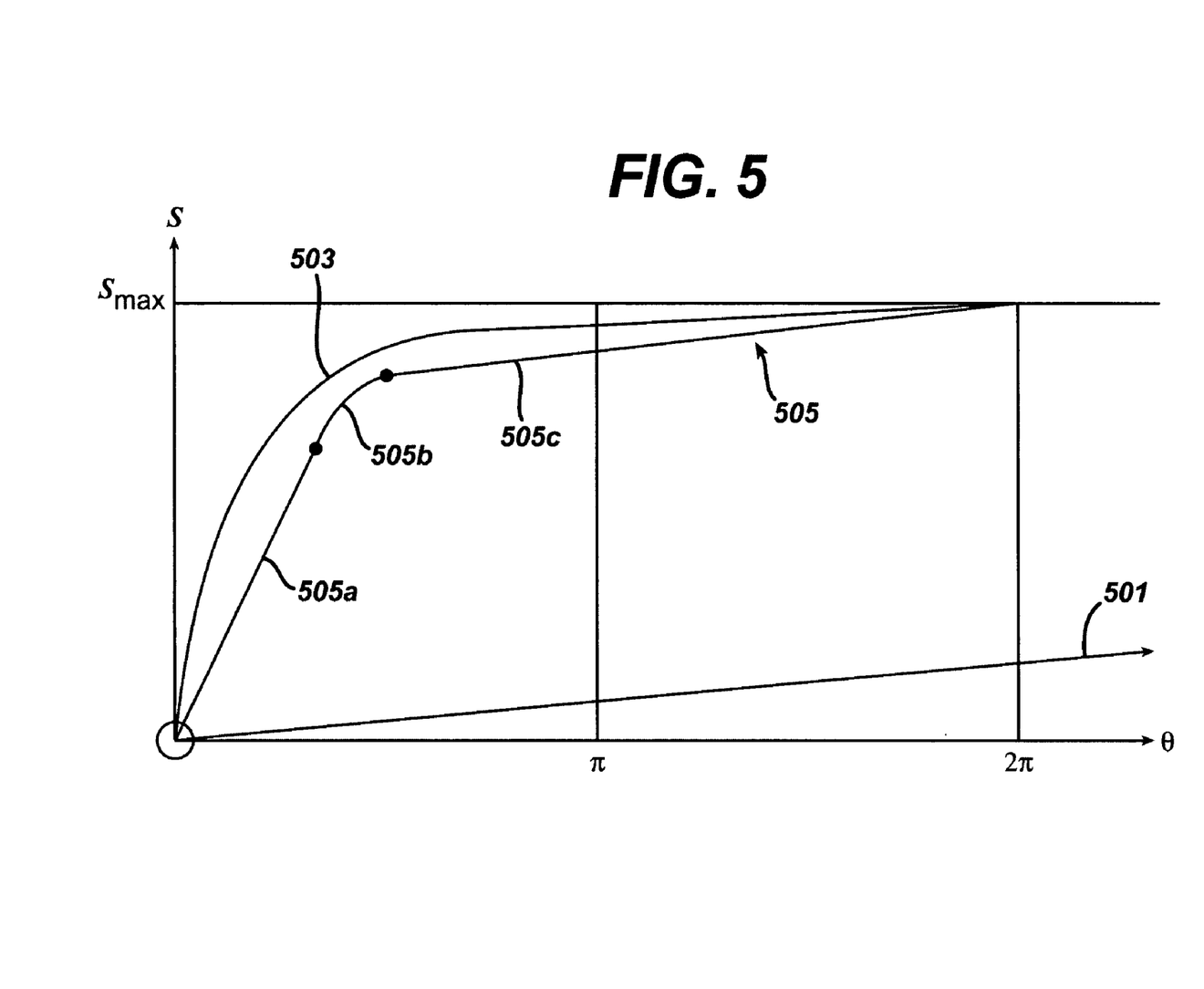
FIG. 5 illustrates various displacement profiles for cams used in tension devices, including two according to the present invention.

Referring now to FIG. 5, a further refinement of the cylindrical cam profile is described. It must be acknowledged that despite advances in numerical control machining techniques, that the profile of cam slot 24 according to a constant force paradigm will present manufacturing challenges, in terms of accuracy and repeatability. Among the reasons for this is that the angle α is continuously changing over the length of the cam slot 24. Therefore, it would be advantageous to simplify the cam profile.

FIG. 5 illustrates the displacement profiles of the prior art, as compared to various embodiments of the present invention. For example, profile 501 illustrates the known prior art, namely a simple lead screw. It will be seen that with on full turn (2π) of the lead screw, the cable displacement does not even approach $S_{max}$, the required tension fiber displacement for full rigidity of the malleable shaft 18. By contrast, profile 503 illustrates a profile that, like the constant force profile, is continuously variable. Profile 505 describes the further refinement. Profile 505 is divided into at least three areas. Area 505a represents a low advantage profile, which can quickly take up tensioning fiber length while forces are low. The cam then enters a transition area 505b, which smoothly transitions from area 505a to area 505c. Finally, area 505c is highly advantaged, to allow the user to comfortably apply the necessary force to complete the transition of the malleable shaft 18 to a rigid state.

The profile 505 improves the ease of manufacturing because area 505a and 505c both exhibit constant screw angles α. Only transitional area 505b requires a change. Further, having the force to the user increase at the end of the range presents other advantages as well. For example, it simulates the traditional end-of-range feel that users of the prior art may be accustomed to when securing those devices.

Figure 6:
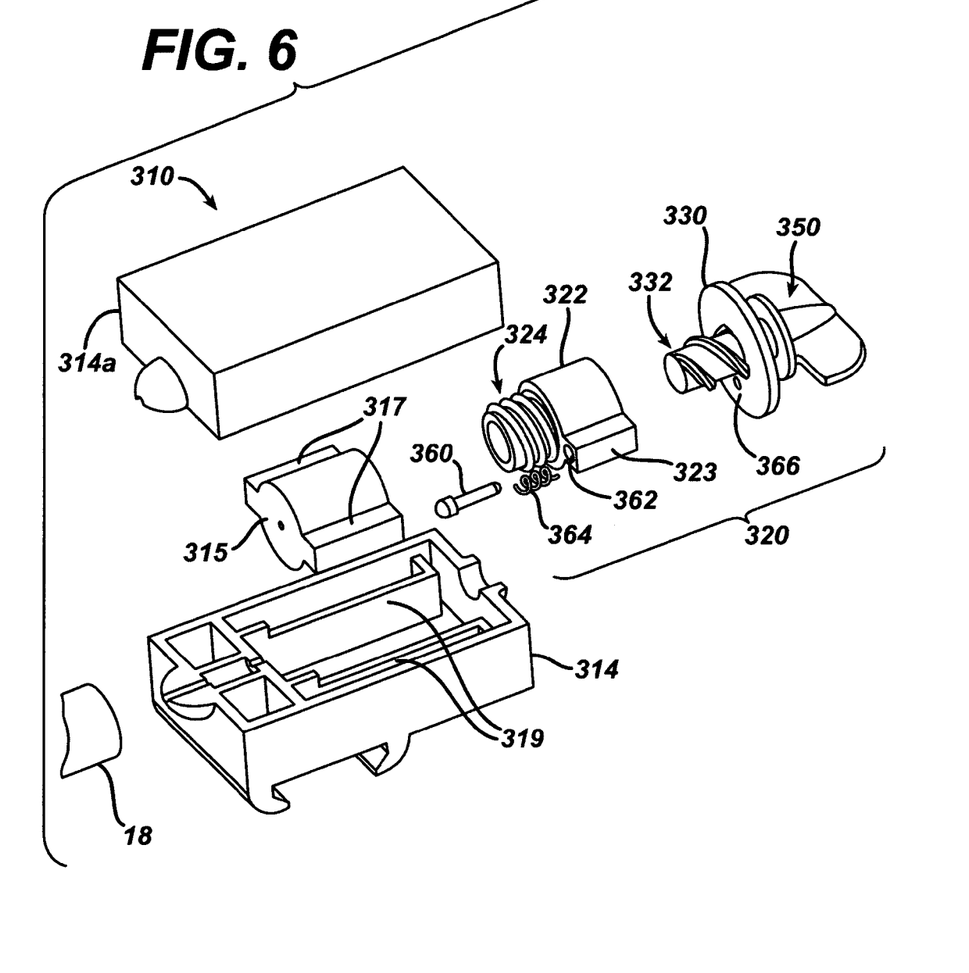
FIG. 6 illustrates a two-stage embodiment of the present invention in an exploded assembly view.
Figure 6A:
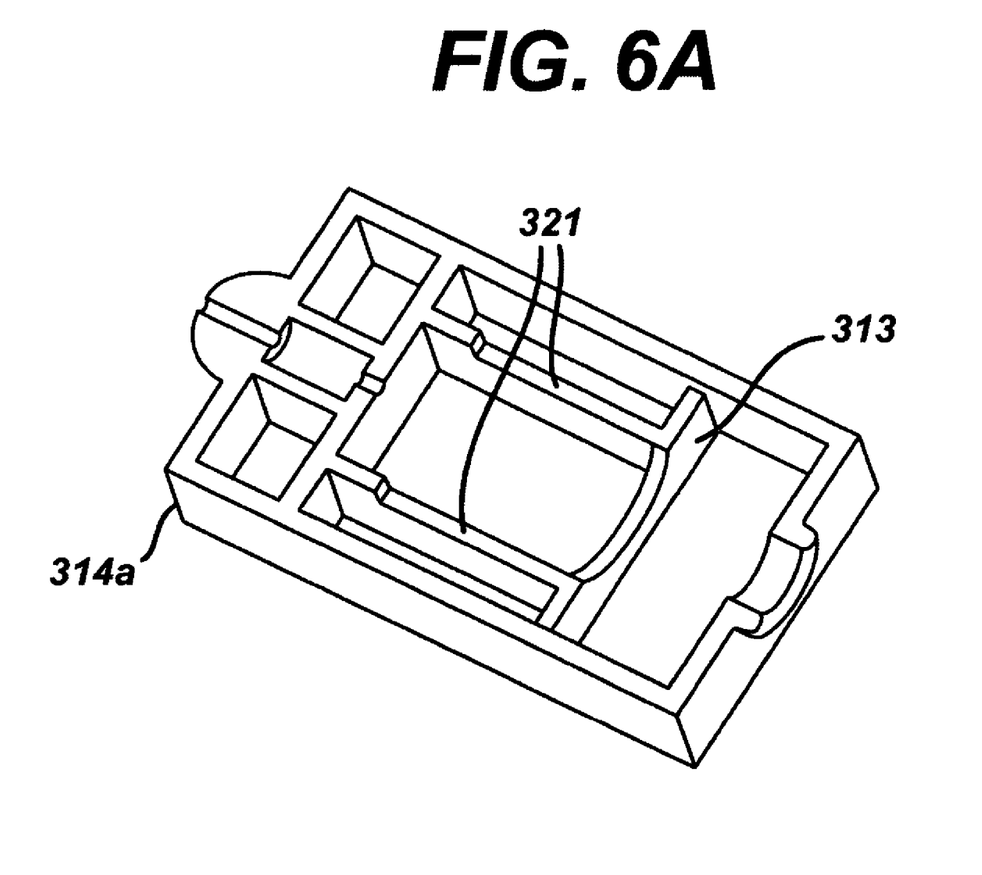
FIG. 6A shows an underside of the upper portion of the embodiment illustrated in FIG. 6.

Referring now to FIG. 6, yet another embodiment, generally 310, of the present invention is shown. In this embodiment, full tensioning of the malleable shaft is accomplished with a two-stage carriage 320. The two-stage carriage 320 has first stage 322 with an exterior thread 324, preferably having a high mechanical advantage. The exterior thread 324 of the first stage 322 mates with a complementary interior thread (not shown) formed within the block 315. Block 315 is operatively connected to the tension fiber and with flanges 317 is constrained to move only axially by ribs 319 in the base 314, and complementary ribs 321 formed in an upper section 314a (See FIG. 6A). Ribs 321 are made shorter, and end at wall 313 to allow the flange 323 of first stage 322 to rotate when the appropriate displacement is achieved.

Carried within the first stage 322 is a second stage 330. The second stage 330 is operatively connected with the tension fiber of the malleable shaft 18. Second stage 330 is formed with an exterior thread 332, preferably having a low mechanical advantage. Exterior thread 332 mates with a complementary interior thread (not shown) formed in the first stage 322. Each of the first stage 322 and second stage 330 are operatively connected to lever 350, respectively, for applying torque to the stages. Alternately, each stage may have an independent lever for actuation.

In operation, the second stage 330 will be torqued with lever 350, whereby the low advantage thread will take up a relatively high portion of the tension fiber displacement quickly, while forces are relatively low. In the turning of second stage 330, first stage 322 and block 315 are pulled axially. When thread 332 of the second stage 330 reaches the end of its travel, preferably within approximately one-half rotation (π) of the second stage 330, torque will be applied to the first stage 322. The pin 360, carried within hole 362 of flange 323, will interface with the wall 313, and against the urging of spring 362, will press through to interface with hole 366 in the second stage 330 as the pin and the hole align. The two stages will then turn together to exercise the travel of the first stage 322.

At the end of travel of the thread 324 of the first stage 322, preferably within approximately one-half rotation (π) of the second stage 330, the transition of the malleable shaft 18 to a rigid state will be complete, and the combined linear displacement of the first stage 322 and second stage 330 will equal $S_{max}$.

Alternately, the respective threads can be chosen to accomplish the full travel of each stage within the range of motion of the longitudinal turning of a human forearm of some portion of the population. Some allowance can be made to accommodate the expected variance among the human population to accommodate a greater percentage of users. Alternately, the respective threads can be chosen to accomplish the full travel of each stage within the one-quarter full rotation (π/2), or one half of the range of motion of the longitudinal turning of a human forearm of some portion of the population.

The present invention has been described herein with respect to certain embodiments. Certain modifications or alterations may be apparent to those skilled in the art without departing from the scope of the invention. The exemplary embodiments are meant to be illustrative, not limiting of the scope of the invention, which is defined by the following claims.

To be secured by United States Letters Patent, what is claimed is:

1. A malleable shaft device for use in surgical procedures comprising:
   a malleable shaft having a tension fiber therein, whereby the malleable shaft transitions from a malleable state to a rigid state when a force is applied to the tension fiber;
   a rotatable cam operatively connected to the tension fiber having a variable-pitch cam groove that interfaces with a cam follower provided within a base of the malleable shaft device, whereby the cam groove and the cam follower cooperate to displace the cam axially when the cam is rotated, applying or relieving force to the tension fiber, said cam groove comprising a first constant pitch portion having a first mechanical advantage, and a second constant pitch portion having a second mechanical advantage greater than the first mechanical advantage; and a lever operatively connected to the rotatable cam for applying torque thereto.

2. The malleable shaft device according to claim 1, wherein the cam groove further comprises a transition portion to smoothly transition between the first and second constant pitch portions.

3. The malleable shaft device according to claim 1, wherein the full axial displacement of the tension fiber necessary to transition the malleable shaft from a malleable state to a rigid state is accomplished in less than about one full rotation ($2\pi$) of the rotatable cam.

4. The malleable shaft device according to claim 1, wherein the full axial displacement of the tension fiber necessary to transition the malleable shaft from a malleable state to a rigid state is accomplished in less than about one-half rotation ($\pi$) of the rotatable cam.

5. The malleable shaft device according to claim 1, wherein the full axial displacement of the tension fiber necessary to transition the malleable shaft from a malleable state to a rigid state is accomplished in less than about the range of motion of the longitudinal turning of a human forearm.

6. The malleable shaft device according to claim 1, wherein the variable-pitch cam grove provides a mechanical advantage that is proportional to the axial displacement of the cam.

7. The malleable shaft device according to claim 1, wherein the variable-pitch cam groove has a cam angle that, at any point along the axial displacement of the rotatable cam, a constant force applied to the lever will transition the malleable shaft from malleable state to rigid state.

8. The malleable shaft device according to claim 1, wherein the lever is a cantilever extending radially outward in one direction from a long axis of the rotatable cam.

9. The malleable shaft device according to claim 1, wherein the lever is a cantilever extending radially outward in two diametrically opposed directions from a long axis of the rotatable cam.

10. A malleable shaft device for use in surgical procedures comprising:
   a malleable shaft having a tension fiber therein, whereby the malleable shaft transitions from a malleable state to a rigid state when a force is applied to the tension fiber;
   a cam plate operatively connected to the tension fiber having a cam groove that interfaces with a cam follower provided within in a base of the malleable shaft device, whereby the cam groove and the cam follower cooperate to displace the cam along the axis of the tension fiber, applying or relieving force to the tension fiber, said cam groove comprising a first portion having a first mechanical advantage, and a second portion having a second mechanical advantage greater than the first mechanical advantage; and
   a lever pivotally connected to the base of the malleable shaft device for applying force to the cam follower.

11. The malleable shaft device according to claim 10, wherein the cam groove is perpendicular to the axis of travel of the cam plate.

12. The malleable shaft device according to claim 11, wherein the cam groove provides a mechanical advantage that is proportional to the axial displacement of the cam plate.

13. The malleable shaft device according to claim 11, wherein the cam groove has a cam angle that, at any point along the axial displacement of the cam plate, a constant force applied to the lever will transition the malleable shaft from malleable state to rigid state.

14. The malleable shaft device according to claim 10, wherein the cam groove further comprises a transition portion to smoothly transition between the first and second portions.

15. A malleable shaft device for use in surgical procedures comprising:
   a malleable shaft having a tension fiber therein, whereby the malleable shaft transitions from a malleable state to a rigid state when a force is applied to the tension fiber;
   a carriage having at least two stages, a first stage interfacing with a base of the malleable shaft device through a screw thread having a first pitch that provides a first mechanical advantage, and a final stage operatively connected to the tension fiber, interfacing with the first stage through a screw thread having a second pitch that provides a second mechanical advantage;
   a first lever operatively connected to the first stage of the carriage and a second lever operatively connected to the final stage of the carriage for applying torque thereto, wherein the first and second levers operate each stage independently of each other.

16. The malleable shaft device according to claim 15, wherein the second mechanical advantage is greater than the first mechanical advantage.

17. The malleable shaft device according to claim 15, wherein the full travel of the first stage is accomplished in less than about one full rotation ($2\pi$) of the first stage.

18. The malleable shaft device according to claim 15, wherein the full travel of the first stage is accomplished in less than about one-half rotation ($\pi$) of the first stage.

19. The malleable shaft device according to claim 15, wherein the full travel of the first stage is accomplished in less than about the range of motion of the longitudinal turning of a human forearm.

20. The malleable shaft device according to claim 15, wherein the full travel of the final stage is accomplished in less than about one full rotation ($2\pi$) of the first stage.

21. The malleable shaft device according to claim 15, wherein the full travel of the final stage is accomplished in less than about one-half rotation ($\pi$) of the first stage.

22. The malleable shaft device according to claim 15, wherein the full travel of the final stage is accomplished in less than about the range of motion of the longitudinal turning of a human forearm.

* * * * *